United States Patent [19]
Chou

[11] 4,175,082
[45] Nov. 20, 1979

[54] PROCESS FOR PREPARING N-CHLOROIMIDES

[75] Inventor: Ta-Sen Chou, Indianapolis, Ind.

[73] Assignee: Eli Lilly and Company, Indianapolis, Ind.

[21] Appl. No.: 861,582

[22] Filed: Dec. 19, 1977

[51] Int. Cl.$^2$ .................. C07D 211/92; C07D 217/24; C07D 487/04; C07D 209/48
[52] U.S. Cl. .......................... 260/326 C; 260/326 HL; 260/326 N; 260/326.5 FM; 260/239.37; 546/66; 546/98; 546/243; 548/210
[58] Field of Search ........ 260/326 HL, 326 C, 326 N, 260/326.5 FM, 301, 281 D, 281 G, 281 H, 239.3 T, 694; 544/94; 281/546, 166, 98

[56] References Cited
U.S. PATENT DOCUMENTS
4,159,266   6/1979   Kukolja ........................ 260/239 A

*Primary Examiner*—Mark L. Berch
*Attorney, Agent, or Firm*—William C. Martens, Jr.; Arthur R. Whate

[57] ABSTRACT

An N-chloroimide is prepared by contacting the corresponding imide with molecular chlorine under substantially non-aqueous conditions and in the presence of an epoxy compound and a tertiary amine.

15 Claims, No Drawings

PROCESS FOR PREPARING N-CHLOROIMIDES

BACKGROUND AND SUMMARY OF THE INVENTION

This invention relates to a process for the manufacture of N-chloroimides. The principal prior art processes for preparing N-chloroimides customarily have involved the use of an aqueous system. In general, such prior art processes for preparing N-chloroimides can be classified as follows:

(1) Chlorination of the corresponding imide using an inorganic hypochlorite in a mixture of acetic acid and water;
(2) Chlorination by passing chlorine into an aqueous solution comprising equivalent amounts of the corresponding imide and a strong base, e.g., sodium hydroxide or potassium hydroxide;
(3) Chlorination of the corresponding imide using t-butyl hypochlorite in a mixture of t-butyl alcohol and water.

Of the above general methods, only method (2) prescribes the use of chlorine itself in the production of the N-chloroimide. However, due to the fact of the aqueous system, this method has been found to have serious drawbacks. First, chlorine is only very slightly soluble in water. Secondly, and more importantly, it is known that an imide, when present in an alkaline aqueous medium such as would result from potassium or sodium hydroxide and water, undergoes rapid hydrolysis. When, for example, phthalimide is subjected to alkaline aqueous conditions, the following decomposition sequence occurs:

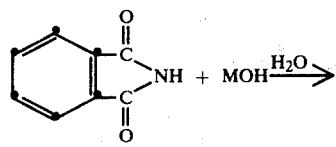

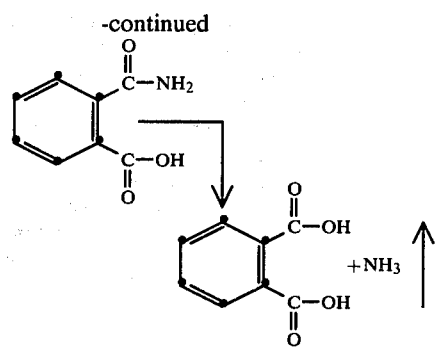

Even more importantly, it has been established [Arthur R. Hurwitz, "Degradation of N-Chlorosuccinimide in Aqueous Solution", Diss. Abst., B, 28 (3), 971 (1967)] that an N-cloroimide product, when present in an aqueous alkaline medium, such as would be the case under the conditions of chlorination provided by method (2) above, degrades with possible formation of the highly explosive and toxic gas, nitrogen trichloride. The following sequences are postulated for the decomposition of N-chlorosucclinimide:

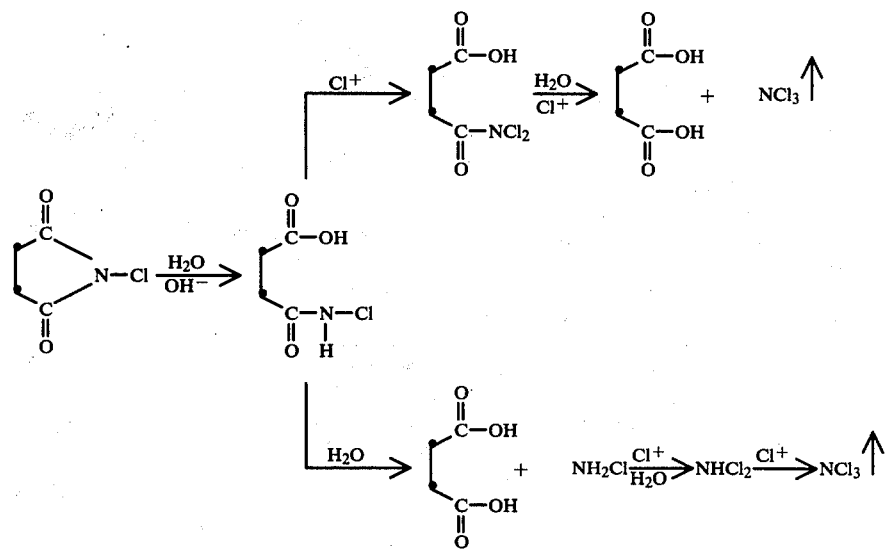

Non-aqueous processes for preparing N-chloro compounds have been few. A process for preparing N-halo-t-alkyl cyanamides is described in U.S. Pat. No. 2,686,203. This process treats a t-alkyl cyanamide with molecular chlorine in an inert solvent and in the presence of a molar equivalent of a halogen acid acceptor, typically pyridine.

Recently, a method for preparing N-chlorophthalimide under substantially non-aqueous reaction conditions was discovered. The aforementioned deficiencies of an aqueous alkaline medium thus were avoided by this method which involves contacting an alkali metal salt of phthalimide with chlorine under non-aqueous conditions in the presence of a halogenated aliphatic hydrocarbon and at a temperature of from about −10° C. to about +40° C. This method is the subject of copending Application Ser. No. 690,471 filed May 27, 1976, now U.S. Pat. 4,082,766.

An even more advantageous method for preparing an N-chloroimide has been discovered. This method is the subject of this invention. It employs a substantially non-aqueous medium and permits use of the imide itself as starting material instead of the previously required alkali metal salt. The N-chloroimide is prepared by contacting the corresponding imide with molecular chlorine at a temperature of from about −10° C. to about +50° C. under substantially non-aqueous conditions and in the presence of (1) an epoxy compound in an amount representing at least about one epoxy moiety per each imide moiety and (2) at least a catalytic amount of a tertiary amine.

DETAILED DESCRIPTION OF THE INVENTION

As indicated hereinabove, this invention is directed to a process for preparing N-chloroimides. The process of this invention involves the interaction of molecular chlorine with the imide corresponding to the intended N-chloroimide product under substantially anhydrous conditions.

The reaction defined by the process of this invention is equimolar in the sense that one mole of chlorine is consumed for each mole of available imide moiety. Therefore, it is highly preferred that at least one mole of chlorine is present per each mole of imide moiety. Even more preferably, about a 10% molar excess of chlorine is brought into contact with the imide. The temperature at which the reaction is carried out generally ranges from about −10° C. to about +50° C. and, preferably, from about −5° C. to about +25° C. The reaction generally is completed after a period of from about 1 hour to about 24 hours, and, preferably, is carried out over a period of from about 3 to 15 hours.

A further feature of the process of this invention is that it can be and is carried out under substantially non-aqueous conditions. It is not intended by the term "substantially non-aqueous conditions" to mean the total absence of water from the reaction system; instead, this term prescribes the exercise of reasonable precautions to ensure its preclusion, including the avoidance of any deliberate addition of water to the reaction medium prior to or during the time in which the reaction is being effected. Amounts of water which are customarily present in such commercial solvents and reactants as may be employed in the process of this invention need not first be removed in order to comply with the "substantially non-aqueous" requirement.

Although it is not an essential feature of the process of this invention, the reaction can be carried out in the presence of an inert organic solvent. By the term "solvent" is intended that medium which partially or completely solubilizes the imide starting material. The term "inert" defines a solvent which generally does not react with the reactants, principally, with the chlorine, under the conditions of the process. Typical such solvents are halogenated aromatic and aliphatic hydrocarbons. Examples of halogenated aromatic hydrocarbons are chlorobenzene, 1,2-dichlorobenzene, 1,4-dichlorobenzene, bromobenzene, and the like. Examples of halogenated aliphatic hydrocarbons are methylene chloride, chloroform, 1,1,2-trichloroethane, 1,2-dichloroethane, 1,1-dichloroethane, 1,1,1-trichloroethane, and the like. Of the above, the halogenated aliphatic hydrocarbons are preferred, and, of these, the preferred solvent is methylene chloride.

The imide starting material employed in the process of this invention is defined broadly as a diacylamine compound and specifically as a compound containing one or more of either or both of the following moieties:

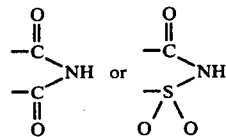

Preferably, these imides do not contain additional functional groups which would be reactive under the conditions of this invention. Typical such functional groups, the presence of which preferably is avoided, are ether, epoxy, hydroxy, amino, sulfide, sulfoxide, carboxyl, and active methylene as well as other such groups having at least one acidic hydrogen.

Illustrations of specific imides which are particularly suitable for the process of this invention are phthalimide, succinimide, saccharin, glutarimide, 3,3-dimethylglutarimide, maleimide, Δ⁴-tetrahydrophthalimide, 3,4,5,6-tetrachlorophthalimide, pyromellitic diimide, benzophenone tetracarboxylic diimide

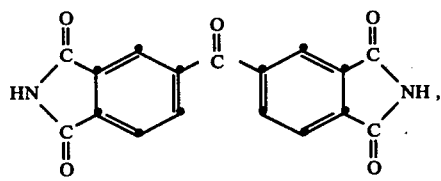

naphthalene 1,4,5,8-tetracarboxylic diimide

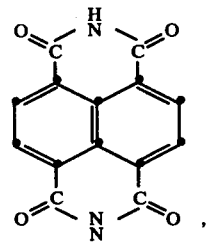

chlorendic imide

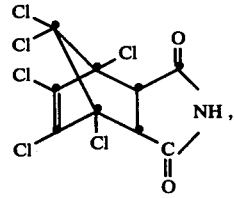

carbonyl salicylimide

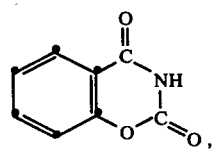

diphenimide

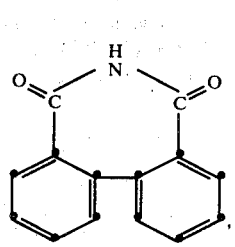

tetrahydrofuran tetracarboxylic diimide

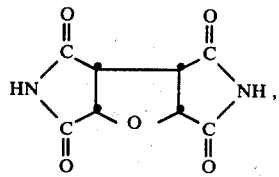

1,8-naphthalimide

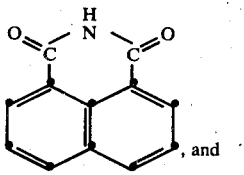

, and bicyclo[2.2.2]oct-7-ene-2,3,5,6-tetracarboxylic-2,3,5,6-diimide

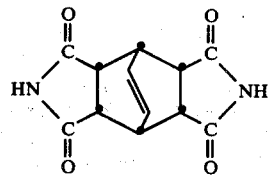

The foregoing is intended to be illustrative only and is indicative of the wide variety of imides, including polyimides, which are suitable for use in the process of this invention. Particularly preferred imides for use in the process of this invention are phthalimide, succinimide, saccharin, and bicyclo[2.2.2]oct-7-ene-2,3,5,6-tetracarboxylic-2,3,5,6-diimide. Of the above, the most preferred imides are phthalimide and bicyclo[2.2.2]oct-7-ene-2,3,5,6-tetracarboxylic-2,3,5,6-diimide.

In addition to the principal reactants, that is, molecular chlorine and the selected imide, the process of this invention contemplates the use of a catalyst and an acid scavenger. The catalyst and scavenger are believed to work in combination to effect removal of the hydrogen chloride by-product which forms in the process of this invention during reaction of the molecular chlorine with the imide. It is believed that the scavenger serves as the ultimate repository for the hydrogen chloride while the catalyst serves as a transfer agent by which the generated hydrogen chloride by-product is made available for pick-up by the scavenger.

In the context of this invention, the scavenger is an epoxy compound. The epoxy compound is present in an amount at least equivalent to the amount of imide starting material. As used in this context, the term "equivalent" means the presence of at least one epoxy moiety per each imide moiety. A large excess of the epoxy compound can be employed without detriment. However, for the sake of convenience and economy, it is preferred that the epoxy compound be present in an amount of from about 1.1 to about 5 equivalents per equivalent of the imide starting material. It is further perferred to employ an epoxy compound having a terminal epoxide group, that is, one containing the moiety

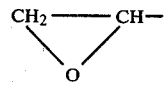

Typical preferred epoxy compounds are ethylene oxide, propylene oxide, 1,2-epoxybutane, butadiene diepoxide, 1,2-epoxy-3-phenoxypropane, 1,4-butanediol diglycidyl ether, 1,2,7,8-diepoxyoctane, and the like. The most preferred epoxy compounds are propylene oxide and 1,2-epoxybutane.

In combination with the scavenger, a catalyst is employed. The catalyst is present in a small but significant quantity, generally from about 0.01 to about 0.04 mole equivalents per equivalent of the imide moiety present in the imide starting material. A larger amount can be employed without detriment. The catalyst which is employed in the process of this invention is a tertiary amine having properties which make it suitable to serve as a catalytic transfer agent. By "catalytic transfer agent" is intended a tertiary amine which achieves transfer of the hydrogen chloride by-product from the site of the protonated N-chloroimide intermediate to the scavenger where it is permitted to react with the scavenger and thereby be removed from the reaction medium. The tertiary amine which is employed has characteristics which permit formation of its hydrochloride salt by deprotonation of the protonated N-chloroimide intermediate. The resulting hydrochloride salt is sufficiently soluble in the reaction medium to permit its transport to the scavenger and sufficiently unstable to permit reaction with the scavenger. Thus, the tertiary amine catalyst has the following characteristics:

(1) ability to generate its hydrochloride salt by reaction with the protonated N-chloroimide intermediate; and (2) generation of a hydrochloride salt, the properties of which include
   (a) at least partial solubility in the reaction medium, and
   (b) sufficient instability to react with the scavenger with removal of the hydrogen chloride and regeneration of the free tertiary amine.

Typical tertiary amines which are suitable for use in the process of this invention are 1,5-diazabicyclo[4.3.0]non-5-ene (DBN), 1,5-diazabicyclo[5.4.0]undec-5-ene (DBU), pyridine, 1,8-bis(dimethylamino)naphthalene, 4-dimethylaminopyridine, N,N-dimethylbenzylamine, diisopropylethylamine, quinoline, 2,4,6-trimethylpyridine, pyrimidine, pyrazine, and the like. In general, pyridine or structural derivatives of pyridine, including quinolines, are preferred for use as catalysts in the process of this invention. Of high preference are pyridine and quinoline, and, especially, quinoline.

An example of a typical preparation of an N-chloroimide in accordance with the process of this invention is as follows:

Phthalimide (0.6 mole) is slurried in methylene chloride (about 1.7 liters of less), and the mixture is chilled to about 0°–5° C. 1,2-Epoxybutane (3.0 moles) and quinoline (0.006 mole) are added. Sufficient chlorine (about 0.66 mole), either as a gas or a liquid, is added by introducing it below the surface of the slurry by means of an inlet tube. The cooling bath then is removed, and the mixture is allowed to warm to a temperature not in excess of about 25° C. After about 1–3 hours, the phthalimide starting material will be gone or nearly gone, and the mixture will have slowly cleared to a yellow solution. A partial vacuum then is applied to the mixture for a few minutes to remove excess chlorine, and amylene (2-methyl-2-butene) is added to take up the remaining chlorine leaving a pale straw-colored reaction mixture. Some exothermicity may be noted as the amylene reacts with the excess chlorine. The excess 1,2-epoxybutane and methylene chloride are removed in vacuo at a temperature not in excess of about 25°–30° C. The N-chlorophthalimide product crystallizes out of solution as the solvent is removed. The volume of the mixture is reduced to approximately 130–150 ml. and comprises mainly product and butylene chlorohydrin. The mixture is chilled in ice for about one hour and filtered, and the collected product is washed with a small volume of cold toluene or petroleum ether. The product is vacuum dried at 25° C. for about 18 hours to obtain the product as colorless to off-white granular crystals in an amount representing a 92–96% yield.

The N-chloroimides produced by the process of this invention are highly useful reagents for carrying out chlorination reactions which require a source of positive chlorine. Examples of such reactions are, for example, oxidation of sulfides, alcohols, amines, and imines; chlorination of amines, reactive aromatic systems, carbonyl compounds having α-hydrogens, and the like.

The examples which follow are illustrative of the process of this invention. They are provided solely for the purpose of illustration and are not intended to be limiting on the broad scope of this invention.

EXAMPLE 1

To 150 ml. of methylene chloride were added 7.35 g. (0.05 mole) of phthalimide, 21.5 ml. (5 equiv.) of 1,2-epoxybutane, and 0.061 g. (0.5 mmoles) of 4-dimethylaminopyridine. The mixture was cooled to 0° C. and saturated with chlorine. The resulting mixture was stirred for 20 hours at room temperature. A sample of the reaction mixture, analyzed by thin-layer chromatography (TLC), indicated that the reaction was not yet complete. The mixture was allowed to stir for an additional 24 hours, and the resulting clear yellow solution was evaporated to obtain crystalline N-chlorophthalimide. The product was vacuum dried to afford 7.7 g. (84.8%) of product. Analysis: (1) Percent Cl+: Theory: 19.6; Found: 18.3. (2) Percent total chlorine: 18.1.

EXAMPLE 2

To 150 ml. of methylene chloride were added 7.35 g. (0.05 mole) of phthalimide and 17.5 ml. (5 equiv.) of propylene oxide. The resulting mixture was cooled to 0° C., 0.13 g. (0.001 mole; 0.02 equiv.) of quinoline was added, and the mixture was saturated with chlorine. The phthalimide began to dissolve within 30 minutes, and after one hour it was nearly all dissolved. Analysis of the sample by TLC at 1.25 hours showed only a trace of starting material. The mixture was subjected to partial vacuum to remove excess chlorine, and a small amount of amylene was added. The resulting mixture then was evaporated to obtain crystalline N-chlorophthalimide. The product was filtered and vacuum dried overnight to give 8.2 g. (90.4%) of product. Analysis: (1) Percent Cl+: Theory: 19.6; Found: 19.3. (2) Percent total chlorine: 19.1.

EXAMPLE 3

Employing the procedure and scale of Example 2, the same reaction was carried out using 0.08 g. (1 mmole; 0.02 equiv.) of pyridine as catalyst. The reaction was virtually complete after about 1.5 hours and afforded 8.0 g. (88.2%) of N-chlorophthalimide. Analysis: (1) Percent Cl+: Theory: 19.6; Found: 19.2. (2) Percent total chlorine: 19.0.

EXAMPLE 4

Employing the procedure and scale of Example 2, the reaction was carried out using 0.12 g. (1 mmole; 0.02 equiv.) of 2,4,6-trimethylpyridine. The reaction was complete after about two hours, and 8.1 g. (89.3%) of N-chlorophthalimide were recovered. Analysis: (1) Percent Cl+: Theory: 19.5; Found: 18.0. (2) Percent total chlorine: 17.2.

EXAMPLE 5

Employing the procedure and scale of Example 2, the reaction was carried out using 0.08 g. (1 mmole; 0.02 equiv.) of pyrimidine. The reaction was complete after two hours, and 8.5 g. (93.7%) of N-chlorophthalimide was recovered. Analysis: (1) Percent Cl+: Theory: 19.5; Found: 19.3. (2) Percent total chlorine: 19.0.

EXAMPLE 6

To 300 ml. of dry methylene chloride were added 9.9 g. (0.1 mole) of succinimide. To the resulting slurry were added 35 ml. (5 equiv.) of propylene oxide and 0.12 g. (1 mmole) of 4-dimethylaminopyridine. The mixture was cooled to 0° C. and saturated with chlorine. The mixture then was stirred for about 18 hours during which it was allowed to warm to room temperature. A sample of the reaction mixture analyzed by TLC indicated little or no starting material. The solvent was slowly evaporated, and the residue was chilled to obtain the crystalline N-chlorosuccinimide product. The product was collected by filtration, washed with a small amount of toluene, and vacuum dried to give 10.6 g. (79.4%) of product as a first crop. Analysis: (1) Percent Cl+: Theory: 26.6; Found: 26.3. (2) Percent total chlorine: 25.9. A second crop of 1.25 g. (9.4%) was recovered. Analysis: (1) Percent Cl+: Theory: 26.6; Found 25.4. (2) Percent total chlorine: 25.1.

EXAMPLE 7

To 150 ml. of methylene chloride were added 9.15 g. (0.05 mole) of saccharin followed by 17.5 ml. (5 equiv.) of propylene oxide and 0.061 g. (0.5 mmole) of 4-dimethylaminopyridine. The mixture was saturated with chlorine and allowed to stir for 4 days. The solvent then was evaporated, and water was added to the residue. The mixture was filtered, and the collected solid was washed with water and vacuum dried to give 9.2 g. (84.6%) of N-chlorosaccharin. Analysis: (1) Percent Cl+: Theory: 16.3; Found: 14.5. (2) Percent total chlorine: 10.2.

EXAMPLE 8

To 150 ml. of dry methylene chloride were added 7.35 g. (50 mmoles) of phthalimide and 17.5 ml. (250 mmoles) of propylene oxide. The mixture was cooled to 0° C., and 0.11 g. (0.5 mmole) of 1,8-bis(dimethylamino)naphthalene was added. An excess of chlorine was added, and the mixture turned bright orange. The mixture was stirred overnight (about 16 hours) at room temperature. The solvent was evaporated in vacuo. Water was added to the resulting crystalline residue, the mixture was filtered, and the collected solid was washed with large volumes of water to give 8.9 g. (98.1%) of N-chlorophthalimide. Analysis: (1) Percent Cl+: Theory: 19.5; Found: 19.1. (2) Percent total chlorine: 18.6.

EXAMPLE 9

Employing the procedure and quantities of Example 8, the reaction was carried out using 0.08 g. (0.5 mmole) of 1,5-diazabicyclo[5.4.0]undec-5-ene (DBU) in place of 1,8-bis-(dimethylamino)naphthalene. N-Chlorophthalimide (8.42 g.; 92.8%) was obtained. Analysis: (1) Percent Cl+: Theory: 19.5; Found: 17.4. (2) Percent total chlorine: 16.9.

EXAMPLE 10

To 150 ml. of methylene chloride were added 7.35 g. (0.05 mole) of phthalimide and 1 drop of DBU. One equiv. of 1,2-epoxy-3-phenoxypropane then was added. The mixture was allowed to react with formation of N-chlorophthalimide.

EXAMPLE 11

Employing the quantities and conditions of Example 9, the reaction was carried out using 0.07 g. (0.5 mmoles) of N,N-dimethylbenzylamine instead of DBU to obtain 8.5 g. (93.7%) of N-chlorophthalimide. Analysis: (1) Percent Cl+: Theory: 19.5; Found: 16.3. (2) Percent of total chlorine: 16.7.

EXAMPLE 12

To 1700 ml. of methylene chloride were added 88.2 g. (0.6 mole) of phthalimide, 210 ml. (5 equiv.) of propylene oxide, and 0.75 g. of (6 mmole) of 4-dimethylaminopyridine. The mixture was cooled to 0° C., and an excess of chlorine was added. The mixture was stirred for a total of about 18 hours, and 5 ml. of amylene then were added. The mixture was evaporated in vacuo to a volume of about 125 ml. with crystallization of the product. The mixture was chilled in ice for about 1.5 hours and then was filtered. The collected product was washed with a small amount of toluene and was vacuum dried overnight to obtain 103.6 g. (95.1%) of N-chlorophthalimide. Analysis: (1) Percent Cl+: Theory: 19.5; Found: 19.1. (2) Percent total chlorine: 19.5.

EXAMPLE 13

To 150 ml. of dry methylene chloride were added 7.35 g. (0.05 mole) of phthalimide followed by 17.5 ml. (5 equiv.) of propylene oxide and 0.065 g. (0.5 mmoles) of diisopropylethylamine. The mixture was cooled to 0° C. and saturated with chlorine. The mixture was stirred for about 24 hours to provide approximately 50% conversion to N-chlorophthalimide.

EXAMPLE 14

To 1,000 ml. of methylene chloride were added 246.2 g. (1 mole) of bicyclo[2.2.2]oct-7-ene-2,3,5,6-tetracarboxylic-2,3,5,6-diimide, 600 ml. of propylene oxide, and 4.7 ml. (0.04 mole) of quinoline. The mixture was cooled to 20° C., and chlorine addition was begun at a rate sufficient to permit maintenance of the temperature of the mixture at 20°-30° C. with ice cooling. After about 40 minutes, the mixture began to thicken, and the chlorine addition rate was reduced. After 2.5 hours the chlorine rate was reduced to a slow stream, and the mixture was stirred gently overnight at about 25°-30° C. In the morning, the reaction mixture (25° C.) was white. The rate of chlorine addition was increased, and, after 2.5 hours, the temperature had increased to 30° C. Chlorine addition was discontinued, and the reaction mixture was concentrated in vacuo to remove excess propylene oxide and chlorine. After about 25 minutes, the temperature had decreased to 5° C. The reaction mixture was filtered rapidly, and the filter cake was washed successively with 500–1000 ml. of methylene chloride, ether, toluene, and pentane. The filter cake then was air-dried for several hours, and the solid was further dried in vacuo at 40°–50° C. overnight to obtain 308.4 g. of N,N'-dichlorobicyclo[2.2.2]-oct-7-ene-2,3,5,6-tetracarboxylic-2,3,5,6-diimide. Analysis: Percent Cl+: Theory: 22.5; Found: 21.7. Some methylene chloride may be retained in the product. This is removed by refluxing the N-chloroimide in toluene.

EXAMPLE 15

To a 1 L. flask were added 125 g. (from a total of 267.7 g.) of phthalimide, 170.6 g. of cold 1,2-epoxybutane, and 2.3 g. of quinoline. The mixture was cooled to 13° C., stirred, and chlorine was added by means of a tube extending beneath the surface of the mixture. The mixture was maintained at 13°–15° C., and about 56 g. of chlorine were added over about 1.5 hours. During the chlorine addition, the mixture first became thicker and then progressively thinner.

The chlorine addition was discontinued, and 96 g. of phthalimide were added to the mixture. The temperature was maintained at 14°–15° C., and chlorine addition again was begun. About 40 g. of the chlorine were added over a period of about 0.75 hours during which time the thick mixture again became thinner.

Chlorine addition was discontinued, and the remainder of the phthalimide, providing a total of 267.7 g., was added to the mixture. Chlorine addition again was begun, and about 30 g. of chlorine were added over a period of about 0.5 hours, the temperature again being maintained at 12°–15° C.

The mixture was allowed to warm to 21° C. over 0.5 hours. A sample of the mixture was removed and analyzed by thin-layer chromatography (TLC). The analysis indicated the presence of some unreacted starting material. The mixture then was cooled to about 12° C., and 6.5 g. of chlorine were added. The mixture again was allowed to warm to temperature and filtered to obtain 322.4 g. of N-chlorophthalimide. Analysis: Percent Cl+: Theory: 19.5; Found: 18.7.

I claim:

1. A process for preparing an N-chloroimide which comprises the step of contacting the corresponding imide containing one or more of either or both of the moieties

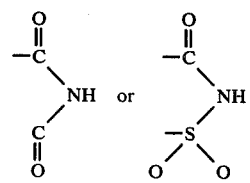

and devoid of additional functional groups which would react under the conditions herein specified with molecular chlorine at a temperature of from about −10° C. to about +50° C. under substantially non-aqueous conditions and in the presence of
  (1) an epoxy compound in an amount representing at least about one epoxy moiety per each imide moiety and (2) at least a catalytic amount of a catalytic transfer agent tertiary amine.

2. Process of claim 1, in which the reaction is carried out in an inert organic solvent.

3. Process of claim 1, in which the reaction is carried out at a temperature of from about −5° C. to about +25° C.

4. Process of claim 2, in which the inert organic solvent is a halogenated aromatic or a halogenated aliphatic hydrocarbon.

5. Process of claim 4, in which the inert organic solvent is a halogenated aliphatic hydrocarbon.

6. Process of claim 5, in which the inert organic solvent is methylene chloride.

7. Process of claim 1, in which the imide is phthalimide.

8. Process of claim 1, in which the imide is bicyclo[2.2.2]oct-7-ene-2,3,5,6-tetracarboxylic-2,3,5,6-diimide.

9. Process of claim 1, in which the epoxy compound has at least one terminal epoxide group.

10. Process of claim 9, in which the epoxy compound is propylene oxide.

11. Process of claim 9, in which the epoxy compound is 1,2-epoxybutane.

12. Process of claim 1, in which the tertiary amine is present in an amount of from about 0.01 to about 0.04 mole equivalents per equivalent of the imide moiety present in the imide starting material.

13. Process of claim 12, in which the tertiary amine is quinoline.

14. Process of claim 12, in which the tertiary amine is pyridine.

15. Process of claim 12, in which the tertiary amine is 4-dimethylaminopyridine.

* * * * *